United States Patent [19]
Tuggle et al.

[11] Patent Number: 5,614,364
[45] Date of Patent: Mar. 25, 1997

[54] GENETIC MARKER FOR IMPROVED MILK PRODUCTION TRAITS IN CATTLE

[75] Inventors: Christopher K. Tuggle; Albert E. Freeman, both of Ames, Iowa

[73] Assignee: Iowa State University Research Foundation, Inc., Ames, Iowa

[21] Appl. No.: 243,543

[22] Filed: May 16, 1994

[51] Int. Cl.$^6$ .............................. C12Q 1/68; C12P 19/34; C07H 21/04; C12N 15/00
[52] U.S. Cl. ............................ 435/6; 435/91.1; 435/91.2; 436/94; 536/23.5; 536/24.33; 536/25.3; 935/76; 935/77; 935/78
[58] Field of Search .............................. 435/6, 91.1, 91.2, 435/183, 240.2, 270; 536/23.5, 24.33, 75.3; 935/1, 5, 8, 9, 76, 77, 78; 436/94

[56] References Cited

PUBLICATIONS

Ingraham, 1988, "A Tissue-Specific Transcription Factor Containing a Homeodomain Specifies a Pituitary Phenotype", *Cell*, vol. 55:519–529.
Wiggans, 1989, "USDA-DHIA Animal Model Genetic Evaluations", *National Cooperative Dairy Herd Improvement Program*, Fact Sheet H–2, 1–8.
Wiggans, 1988, "Implementation of an Animal Model for Genetic Evaluation of Dairy Cattle in the United States", pp. 54–69.
Voss, 1992, "Anterior Pituitary Development: Short Tales From Dwarf Mice", *Cell*, vol. 70:527–530.
Steinfelder, 1991, "Thyrotropin–Releasing Hormone Regulation of Human TSHB Expression: Role of a Pituitary–Specific Transcription Factor (Pit–1/GHF–1) and Potential Interaction With a Thyroid Hormone–Inhibitory Element", *Proc. Natl. Acad. Sci. USA*, vol. 88:3130–3134.
Bodner, 1988, "The Pituitary–Specific Transcription Factor GHF–1 Is a Homeobox–Containing Protein", *Cell*, vol. 55:505–518.
Welper, 1992, "Genetic Parameters for Yield Traits of Holsteins, Including Lactose and Somatic Cell Score", *J. Dairy Sci.* 57:1342–1348.
Pfäffle, 1992, "Mutation of the POU–Specific Domain of Pit–1 and Hypopituitarism Without Pituitary Hypoplasia", *Science* 257:1118–1121.
Radovick, 1992, "A Mutation in the POU–Homeodomain of Pit–1 Responsible for Combined Pituitary Hormone Defiency", *Science* 257:1115–1118.
Ohta, 1992, "Mutations in the PIT–1 Gene in Children With Combined Pituitary Hormone Deficiency", *Biochemical and Biophysical Research Communications*, pp. 851–855.
Li, 1990, "Dwarf Locus Mutants Lacking Three Pituitary Cell Types Result From Mutations in the POU–Domain Gene PIT–1", *Nature* 347:528–533.
Tsukahara et alii, *Environ Med (Nagoya)*, 36 (0), 1992, pp. 55–58; *Abstract Only* New England BioLabs® 1988–1989 Catalog, p. 62.

*Primary Examiner*—Bradley L. Sisson
*Attorney, Agent, or Firm*—Zarley, McKee, Thomte, Voorhees, & Sease

[57] ABSTRACT

Genetic markers in the bovine PIT-1 gene are disclosed which are associated with increased milk production and increased protein and fat content in cattle. Further, novel sequence data from intron regions of the gene are disclosed which may be used in a PCR test to screen for the presence of the marker.

12 Claims, 11 Drawing Sheets

```
1    CTGAATCAGTCCCTGGGTTGGGAAGATCCCCTGGAGCTGGGAACAACCTACCNAACCAGA    60
61   TTCTGGCCTGGAGAATTCCATGTACTGTATAGTCCATGGGGTTGCAAAGAATAGTCTGAC   120
121  TACACTTATATATTAGGTTTATAAAAATGATTCATGTATAATTACTACACAGTATATAGCCCCAGT   180
181  GCCAAAAAAATAAATCTGGACACATTAAAAAGCATTTCACTACTTTATACCTATGCTACA   240
241  TTGTCTAGAAACTTTTCTTATATATTTTTGCAAAGTGTGTTTAACACATTTATCCAGTTT   300
301  GGCTAAATATGAATGGCAGATGTTCCTATCTGAATTCTTTTGGCTTCTAAAATATTAACT   360
```

FIG. 3A

```
361  TATTAACTAGAAGGAAGTTTTTAAAATACTAGACAATTCTACACTGAATAACCTTACTG   419

420  TTATTCTAAATTGCTAACAAATATATCGTTAAAAGCAATATTTAATAGTTGACAAAAATA   479

480  CTACACAAATTTATACAATAGTGGAGCCAAATCAGTGTTTCTTGCACCACTGAAGCTGAT   539

540  GGCCTTTGTTATTCTTTCACAGGATACACCCAGACAAATGTTGGGGAAGCTCTGGCAGCT   599
                              GlyTyrThrGlnThrAsnValGlyGluAlaLeuAlaAla

600  GTGCATGGCTCTGAATTCAGTCAAACAACTATCTGCCGATTTGAAAACCTGCAGCTCAGC   659
     ValHisGlySerGluPheSerGlnThrThrIleCysArgPheGluAsnLeuGlnLeuSer
```

FIG. 3B

```
660  TTCAAAAATGCATGCAAACTAAAAGCAATATTATCCAAATGGCTGGAGGAAGCCGAGCAA  719
     PheLysAsnAlaCysLysLeuLysAlaIleLeuSerLysTrpLeuGluGluAlaGluGln

720  GTAGGAGGTACAAAAGCTGTGTTTCTGGAAACAGTGATGTTTAACCTAAAAACAATGGT   779
     ValGly

780  TTCCCTCAGTTGAATTTGTGCTAAAAGCGAGAGGTTTGAAGTTTGGTTTGATTTTCTCT   839

840  TTGACATGAAAAATAAGTATCTTGTTTCATCACACTATGAAGAAAAGCAAGGCCAGTGAA  899

900  AGTGTAGAAAATAAATTTATTGAGAAGGTAAATAATGAGAGAATAAAATATATAGGGAAAG 959

960  TTTCTACACAATGTGGCATAGGTGTGAAGTGGTGAAATGATTC  1002
```

*FIG. 3C*

```
  1  ATGACTTCTAGCATTTCAAGCCAGATTGTTCAATTTATCTTTTTGTAGTTTCCGTGAGGC
 61  TCATGGAGGAATTGCTAATANACAGGTTTTGTTTTGGNTGGNTAGTTGTACACTAAACAT
121  TTCAATAACCTGAGTTCTGGGGACATTTAGAAATGCATACAGAATTATTTTCTTCTCAG
181  TAAGTCAGTGCCCTCTTGTGGCAGAAAGTGGATAAACAATGTCGGGGTTCCCTCCCTAAT
241  TTCTTCCCTGTGACTCTGGTAAAAGGAGCCTACATGAGACAAGCATCTAAATGTTCAAAAA
301  AACTTCACATTTATTATTGTTGAAAAGCTTTGAAGGTGTTTCAGCGTCTTTAGGTTTCC
```

FIG. 4A

```
361  TTTTTACGTTAATGTTAGTACTAATATTTAGGAAATGTAACCTAACTTGATTTTAATGGG

421  CCTAAACCATCATCTCCCTTCTTTCCTGCCAACTCCCCACTCCCCAGTATTGCTGCTAAA
                                                 SerIleAlaAlaLys

481  GACGCCCTGGAGAGACACTTTGGAGAACAGAATAAGCCTTCCTCTCAGGAGATCCTGCGG
     AspAlaLeuGluArgHisPheGlyGluGlnAsnLysProSerSerGlnGluIleLeuArg

541  ATGGCTGAAGAAAACCTGGAGAAAGAAGTGGTGAGGGTTTGGTTTTGTAACCGAAGG
     MetAlaGluGluAsnLeuGluLysGluValValArgValTrpPheCysAsnArgArg

601  CAGAGAGAAAAACGGGTGAAGACAAGCCTAAATCAGAGTTTATTACTATTTCTAAGGAG
     GlnArgGluLysArgValLysThrSerLeuAsnGlnSerLeuPheThrIleSerLysGlu
                                       G
```

FIG. 4B

```
661  CATCTCGAATGCAGAGATAGGCTCTCCTATTGTGTAATAGCGAGTGTTTCTACTTTTCATTC
     HisLeuGluCysArgEnd

721  CTTTCTCTCTCCAGCCAAAATAGTTATTGGTTAGCTTCAAAAATCACATC

781  AGTAATTTTGGCAGAAGTGTTTCTTTTCTACTTTAAAAATAAATACAATTTAAATTATGT

841  TGATGAATTATTCTCAGAAGGCACATTGTACATTTTAAGCCAAAGACTAATAGGATTAAA

901  ACAATGATTCTGTCCCTTTCACTATATCTTTCCCTATCTCTCCCTAACACACACACACAC

961  ACACACACACAG  972
```

FIG. 4C

GENETIC MARKER FOR IMPROVED MILK PRODUCTION TRAITS IN CATTLE

GRANT REFERENCE

Work for this invention was funded in part by a grant from United States Department of Agriculture, Apricultural Research Service Grant #59-3K95-3-126. The Government may have certain rights in this invention.

FIELD OF THE INVENTION

The present invention relates to a method of genetically evaluating cattle by assaying for the presence of at least one genetic marker which is indicative of improved milk production, including milk yield and milk composition.

BACKGROUND OF THE INVENTION

With the increasing costs associated with animal breeding and artificial insemination, each cow obtained by a dairy producer for production of milk products represents an enormous investment of both time and money. Traditional methods of insuring cow performance have included standard breeding techniques in which sire progenies are studied. Milk production ratings (transmitting abilities) are then used to guide further breeding.

One such particularly successful breeding family is the Holstein line derived from Carlin-M Ivenhoe Bell. It has been estimated currently that more than 25% of the highest total performance index Holstein bulls in the United States are progenies of this individual. This standard technique, however, requires years to evaluate the true genetic value by progeny testing each bull. Many cows must be bred and give birth to offspring. The females must be raised, bred, allowed to give birth and finally milked for a minimum length of time to measure their phenotypic traits.

Further, complex gene action and interactions among genes serve to complicate this objective. Selection based purely on phenotypic characteristics does not efficiently take into account such genetic variability. Thus, it is clear a need exists in the art for a method of genetically evaluating cattle to enable breeders to more accurately select those which not only phenotypically express desirable traits but those which express favorable underlying genetic criteria.

The ability to follow a specific favorable genetic allele involves the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal; or even earlier as technology is developing to test embryos in vitro if very early embryos are collected.

For example, currently selected females are superovulated, eggs are collected, in vitro fertilized using semen from superior males and implanted into other females allowing for use of the superior genetics of the female (as well as the male) without having to wait for her to give birth to one calf at a time. This would be a modification of a selection scheme, termed multiple ovulation and embryo transfer (MOET) and can be used with genetic marker technology in that developing blastomeres at the 4–8 cell stage can be assayed by PCR for presence of the marker, and selection decisions made accordingly.

Marker-assisted selection could thus lower the high cost of progeny testing currently used to prove sires, since young bulls that are determined by genetic testing to have undesirable markers would never be progeny tested and young bull progeny could be evaluated immediately after birth for the presence/absence of the marker.

In general the standard methodology includes extraction of DNA, digestion with restriction enzymes, separation of the resulting fragments, hybridization to radio-labeled probe, and finally correlation of identified polymorphisms with milk production traits to identify a marker to aid in selection. A newer technology, using the polymerase chain reaction (PCR*) to amplify the relevant gene fragment for further analysis, has also become available. Such PCR technology speeds the analysis, since (1) less genetic material (blood or serum sample) is necessary; (2) the hybridization step to detect specific gene fragments are avoided; (3) costs of some materials (radioactive label, x-ray film) are eliminated, decreasing overall costs of analysis; and (4) remaining analysis steps are very rapid. Genetic markers have been found which indicate the presence of bovine leukocyte adhesion deficiency, markers have been located within the bovine prolactin gene, and with κ casein which are associated with superior milk products and markers have even been used to detect bovine mitochondrial DNA variants which are associated with improved dairy cow performance.

One attempt to improve resulting cattle performance has included boosting the level of growth hormones via introduction of additional hormones. A notable example is use of bovine growth hormone, which has recently gained FDA approval. This has been made possible by the cloning and isolation of genes that express such proteins and then adding the resulting products of these commercially produced proteins to feeds, drugs, etc. This method of boosting production of essential proteins however is inherently limited by the underlying genetics of the animal and does not offer anything in the way of selection of genetically superior animals for optimum genetic capabilities.

Further public acceptance of injecting growth hormone remains to be seen. Qualified administration of multiple injections keep costs high and animals which are sick cannot be so treated. The results of bovine growth hormone injection include an increase in overall milk production, with no change in milk composition. This is significant because a dairy producer is paid on the basis of three milk characteristics, total volume of milk, total pounds of fat in the milk, and total pounds of protein in the milk, thus quality is as important as quantity. Producers are paid more for protein than fat. Thus it can be seen that there is a continuing need for means of efficiently selecting and breeding cattle for improved milk production without concomitant decrease in milk composition, particularly protein.

It is an object of the present invention to provide a genetic marker within the bovine PIT-1 gene which is indicative of increased milk yield and milk composition.

Yet another object of the present invention is to provide an assay for determining the presence of this genetic marker.

Yet another object is to provide a method of evaluating cattle that increases accuracy of selection and breeding methods.

Yet another object is to provide a PCR amplification test which will greatly expedite the determination of presence of the marker.

Other objectives and advantages of the invention will be apparent from the detailed description of the invention which follows.

SUMMARY OF THE INVENTION

This invention relates to the discovery of polymorphisms within the PIT-1 gene which are associated with increased milk yield and improved milk composition. According to the invention the HinfI restriction pattern which identifies at least one polymorphism is used to assay for the presence or absence of a marker associated with desirable milk traits. The non marker genotype consists of at least one polymorphism within exon 6 of bovine PIT-1 which creates an additional HinfI site. The marker genotype, with no additional HinfI site, is associated with an average 13.2% increase in milk production as well as an average 17.2% increase in total protein. The invention includes assays for detection of the marker as well as sequence characterization of one of the polymorphisms and includes novel intron sequences in the PIT-1 gene which may be used to design amplification primers for such an assay.

DESCRIPTION OF THE DRAWINGS

FIG. 3A is the sequence of bovine PIT-1 exon 4 and novel flanking DNA. (SEQ ID NO: 1) N represents a position where the sequence has not yet been determined. HinfI recognition sites are underlined. (HinfI has a degenerate recognition sequence of 5'-GANTC-3').

FIG. 3B is the continuation of the sequences of bovine PIT-1 exon 4 and novel flanking DNA.

FIG. 3C is the continuation of the sequence of bovine PIT-4 exon 4 and novel flanking DNA from FIG. 3B.

FIG. 4A is the sequence of bovine PIT-1 exon 6 and flanking DNA and is presented the same way as FIG. 3. (SEQ ID NO: 2)

FIG. 4B a continuation of the sequence of bovine PIT-1 exon 6 and flanking DNA from FIG. 4A.

FIG. 4C is a continuation of the sequence of bovine PIT-1 exon 6 and flanking DNA from FIG. 4B.

DETAILED DESCRIPTION OF THE INVENTION

PIT-1 protein functions by binding to and transactivating the promoters of both growth hormone (GH) and prolactin (PRL) genes and that of the PIT-1 gene itself reviewed in (Voss, J. W. and M. G. Rosenfeld, (1992) Anterior Pituitary Development: Short Tales From Dwarf Mice. CELL 70: 525–530). PIT-1 has been shown to mediate both thyrotropin-releasing hormone (TRH) and cAMP stimulation of the prolactin and thyrotropin b-subunit (TSHβ) genes. (Steinfelder et al., (1991) Thyrotropin-Releasing Hormone Regulation of Human TSHB Expression: Role of a Pituitary-Specific Transcription Factor (Pit-1/GHF-1) and Potential Interaction With a Thyroid Hormone-Inhibitory Element. PROC NATL ACAD SCI USA 88:3130–3134). The PIT-1 gene and protein has been found in several mammalian species including mouse, rat, bovine, human and swine.

PIT-1 mRNA transcripts have been found in all five cell types of the mature pituitary gland, but the PIT-1 protein has been detected in only three cell types (lactotrophs, somatotrophs and thyrotrophs) of the anterior pituitary gland (Ingraham et al., (1988) A Tissue-Specific Transcription Factor Containing a Homeodomain Specifies a Pituitary Phenotype. CELL 55: 519–529).

As earlier indicated the PIT-1 gene regulates expression of the growth hormone gene and the prolactin gene from the pituitary gland. The bovine cDNA for PIT-1 has been sequenced, however, genomic sequences including intron regions have not yet been reported. The cDNA sequence of bovine PIT-1 in the literature has not been fully determined; several sequence regions are ambiguous (Bodner, et al., (1988) The Pituitary-Specific Transcription Factor GHF-1 is a Homeobox-Cintaining Protein. CELL 55: 505–518). According to the present invention, polymorphisms in the PIT-1 gene have been located, and this genetic variability is associated phenotypically with milk production traits.

Figure 1:
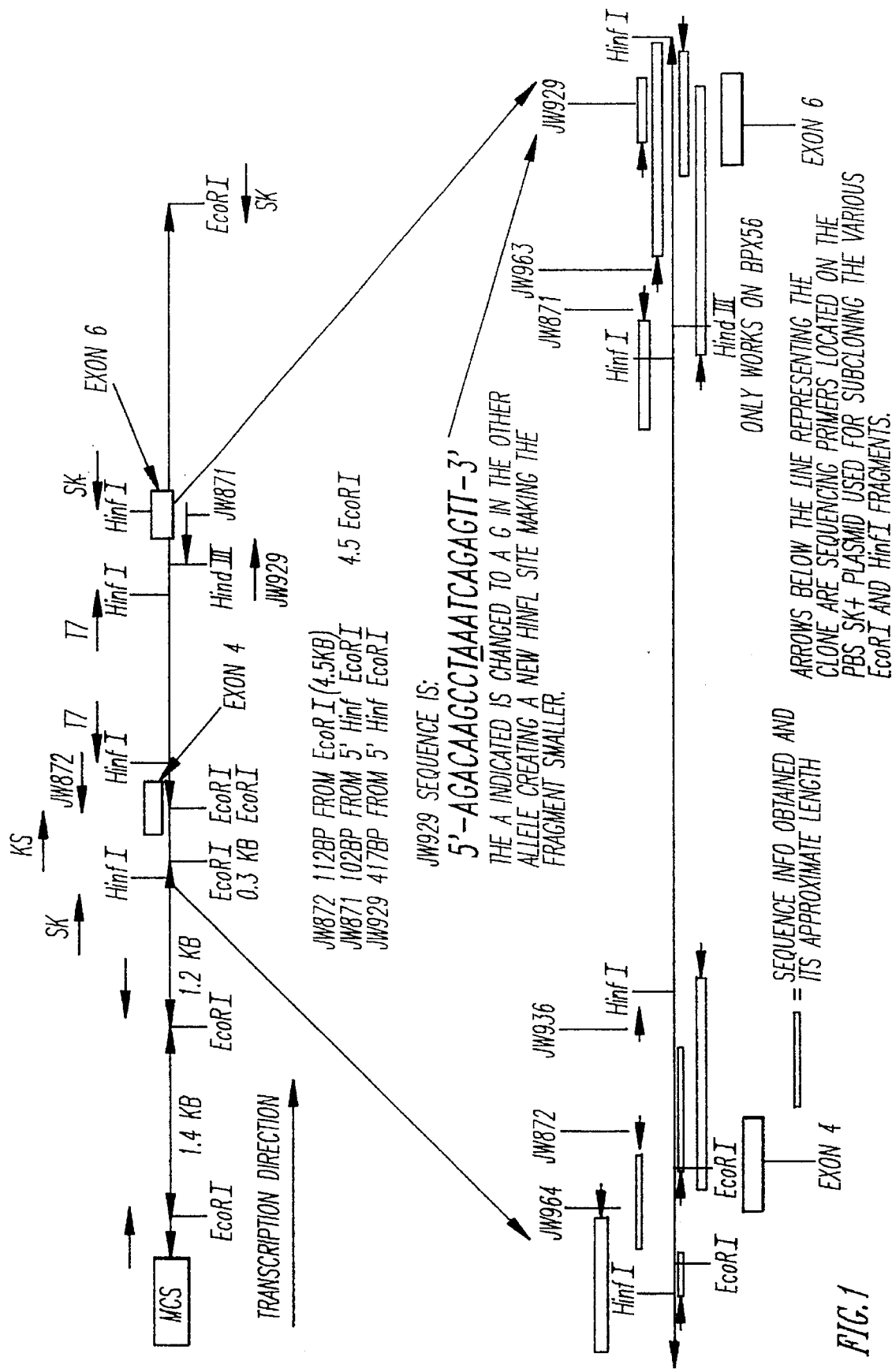
FIG. 1 is a restriction map of the bovine genomic PIT-1 region.

In one embodiment of the invention an assay is provided for detection of presence of a desirable genotype. The assay involves exposing the genomic DNA purified from blood or semen, to a restriction enzyme (e.g. HinfI) so as to yield gene fragments of varying lengths; separating at least some of the fragments from others (e.g. using electrophoresis); then hybridizing a cDNA probe (e.g. radio-labeled cDNA probes) that contains all or at least a portion of bovine PIT-1 gene cDNA sequence to the separated fragments; and finally comparing the results of the hybridization with assay results for a bovine gene sequence known to have the marker or a bovine gene sequence known not to have the marker. Selection and use of probes for detection of PIT sequences based on the known and disclosed PIT-1 sequences and the restriction map, FIG. 1 is generally known to those of skill in the art. The probe may be any sequence which will hybridize to the separated digestion products, and allow for detection.

Also polymerase chain amplification methodology can be used based on sequence data to amplify the area around the polymorphism, using primers which will obviate the need for a probe to detect digested fragments.

Yet another embodiment of the invention provides a kit for assaying for the presence in a PIT-1 gene sequence of a genetic marker within the exon 6 sequence. The marker being indicative of an inheritable trait of increased milk production and composition. The kit in a preferred embodiment also includes novel PCR primers comprising 12–30 contiguous bases on either side of the polymorphism to provide an amplification system allowing for detection of the exon 6 HinfI polymorphism by PCR and HinfI digestion of PCR products.

Yet another embodiment comprises a breeding method whereby an assay of the above type is conducted on a plurality of gene sequences from different bovine embryos to be selected from and based on the results, certain cattle are either selected or dropped out of the breeding program.

According to the invention, polymorphisms in the PIT-1 gene identifiable by the HinfI restriction pattern and use of a bovine PIT-1 cDNA probe, although any sequence which will hybridize to the fragments may be used as a probe, are disclosed. As is known in the art, restriction patterns are not exact determinants of the size of fragments and are only approximate. The polymorphisms are identifiable by two bands, one at approximately 800 base pairs (bp) and one at approximately 650 bp for one genotype; two bands, one at approximately 750 bp and one at approximately 300 bp for another genotype; and finally all four bands. See FIG. 2. The sequences identified by the 800 and 650 bands have been obtained. The non-marker genotype includes an additional HinfI site in exon 6 which generates a smaller (300 bp) band. The 800/750 RFLP pattern has not yet been characterized at the nucleic acid level. The marker, identifiable by the 800/650 bands is associated with improved milk production rates including increase of total protein and fat content.

This is an unexpected result as there is traditionally an inverse relationship between overall milk production; and milk components such as fat and protein percentages. Quite unexpectedly cows with the marker have been shown to have an average 13.2% increase in milk production and a 17.2% increase in total protein yield and a 12.6% increase in total fat yield.

In addition, at least one of the marker polymorphisms associated with the pattern has been identified at the nucleotide level. One of the polymorphic HinfI sites located within exon 6 was sequenced along with the general surrounding intronic area. See SEQ ID NO: 2. Further, other novel intronic sequences have been disclosed, which are in the general area of exon 4. The sequences surrounding exon 6 have facilitated the development of a PCR test in which a primer of about 12–30 contiguous bases taken from the sequence immediately adjacent to the polymorphic loci is used in connection with a polymerase chain reaction to greatly amplify the region before treatment with the HinfI restriction enzyme.

From sequence data it was observed that in the non-marker genotype a guanine is substituted for an adenine at position 630 in SEQ ID NO: 2, nt 165 in exon 6. The PCR test for the exon 6 HinfI polymorphism used a 5' primer of 5'AAACCATCATCTCCCTTCCTT3' SEQ ID NO: 3; and a 3' primer of 5'AATGTACAATGTGCCTTCTGAG3' SEQ ID NO: 4. The resulting 451 bp amplified product, when digested with HinfI, results in a 244 bp and a 207 bp fragment for the non-marker genotype. See FIGS. 1 and 6 (generation of the additional HinfI site by a transition event). Thus, complete cutting of the PCR product indicates that the animal does not have any copies of the marker allele (homozygous for the nonmarker); 50% cutting indicates the animal has one copy of each genotype (heterozygous); and no cutting indicates the animal has two copies of the marker gene (See FIG. 6).

EXAMPLE 1

Association of Marker with Increased Cattle Performance

To confirm the association of the markers of the invention with increased dairy performance, presence or absence of the marker was correlated with overall milk production as well as fat and protein content of milk. Dairy cows in the study were from a group maintained at Iowa State University which is scientifically designed to genetically mimic the United States Holstein population.

Heifers for the foundation herd were originally purchased in 1968 from 38 breeders throughout Iowa to keep the herd as genetically broad based as possible. Cows were bred artificially to sires from commercial artificial insemination organizations allowing a continuous influx of nuclear genes. Frequencies of bovine lymphocyte antigen phenotypes for the herd were similar to frequencies in the U.S. Holstein population further indicating that the nuclear genes are likely representative of the entire U.S. Holstein population. Females have been assigned to groups and artificially mated to bulls with either high or average estimated additive genetic transmitting ability for pounds of fat plus pounds of protein.

The polymorphisms were identified using standard techniques (Sambrook, et al. (1989) Molecular Cloning-A Laboratory Manual. 2nd Edition, Cold Spring Harbor Laboratory Press, Cold Spring Harbor, N.Y.). Samples of genomic DNA were obtained and purified. The sample was exposed to the restriction enzyme HinfI and digested to completion to cut the DNA to fragments which were separated by agarose gel electrophoresis, transferred to membranes and hybridized to radiolabeled PIT-1 cDNA as a probe to detect the specific pattern of PIT-1 DNA fragments. Southern blot hybridization was performed per standard procedures known to those of skill in the art with the following specific details. All blot material used was nitrocellulose (BA-S 85 from Schleicher and Schuell, Inc.). Prepared membranes were prehybridized at 65° C. for 2–3 hours in the following solution (used at 30 mls per 20 cm×20 cm membrane):

5x Denhardt's reagent 0.5% Na SDS

6x SSC 10 ug/ml sheared, denatured salmon sperm DNA The bovine PIT-1 cDNA probe was labelled with $\alpha$-$^{32}$p-dCTP using standard methods. At the end of the prehybridization time, the labelled probe was boiled and added to the prehybridization. The hybridization was allowed to proceed for 16–20 hours at 65° C. The hybridization solution was then removed and the membrane washed twice for 15 minutes each time in 0.5×SSC and 0.1% Na SDS at 60°–65° C. The filters were allowed to airdry and then exposed to X-ray film with intensifying screens per standard procedures.

From this maintained herd, 115 cows with 253 lactational records were analyzed to correlate the marker with phenotypic milk production. The marker was present in about 40% of the animals.

The statistical model applied to the lactational records that was used to estimate the difference between cows that had the marker and those that did not have the marker was a mixed model that included all relationships among the 115 cows. This method is widely used and accepted by those of skill in the art. Generally it can be described as:

$$Y = x\beta + Zu + e$$

where

Y=a vector of lactational records x=an incidence matrix relating the observations in Y to the fixed effects in $\beta$ $\beta$=a vector of fixed effects composed of year-season of calving, parities, selection lines, and PIT-1 genotypes (marker/no marker)

u=a vector of random cow (a) and permanent environmental (pe) effects

Z=an incidence matrix relating the observations in Y to the random effects in u e=a random residual Priors ($\sigma^2_e/\sigma^2_a, \sigma^2_e/\sigma^2_{pe}$) for production traits were those used for the National Sire Analysis (variance ratios were obtained from Wiggams, G. R. and P. M. Van Randen (1989) USDA-AIPL Animal Model Evaluations. Nat. Coop. DHI Program Handbook, Factsheet H-2, Extension Service, USDA, Washington, D.C.). This is a well known model that is used extensively by animal breeders and is used for national sire and cow evaluation (G. W. Wiggams, I. Mistal, and L. D. Van Vleck (1988) Implementation of an Animal Model for Genetic Evaluation of Dairy Cattle in the United States. J. Dairy Science (Supplement 2) 71:54.

When the 115 cows from the group of combined fat plus protein (CFP)(those representative of current Holstein population) were considered for presence of the marker, the statistical association data is indicated in Table 1.

TABLE 1

Analysis of data for the PIT-1 genotype
(Effect of PIT-1 genotype per
cow per lactation period)

| Data Set | Average Milk Production (lbs) | Average Fat Production (lbs) | Average Protein Production (lbs) | % Fat | % Protein |
|---|---|---|---|---|---|
| Cows without PIT-1 genotype | 20,607* | 674 | 630.5 | 3.27 | 3.06 |
| Cows with PIT-1 genotype | 22,804* | 746 | 721.5 | 3.27 | 3.16 |
| Difference due to PIT-1 | 2,197 | 72 | 91 | 0 | 0.10 |

Results obtained using National Sire Analysis variance ratios
*Values in table are herd mean plus or minus ½ of the effect of PIT-1 marker From the table it can be seen the advantage of the marker is an increase in average total milk production of 2197 pounds per cow per lactation, an increase in total average protein of 91 pounds per cow per lactation, and an increase in average total fat of 72 pounds per cow per lactation. Expressed as a percentage of actual herd average these are milk 13.2% increase, fat 12.6% increase and protein 17.2% increase. There is a significant difference in favor of cows with the marker for increase in pounds of protein (P<0.1). Thus the probability of this occurring by chance is less than 10%. For pounds of fat increase the significance level is 0.1<P<0.2. Thus the probability of difference attributable to the presence of the marker being due to chance is thus between 10% and 20%. Current breeding and selection methods traditionally show gains of 6 lbs. of protein per lactational period per year. As can be seen this marker gives an average increase of 91 lbs. of protein per lactation, per cow.

Also important is the surprising result that cows with the marker maintained fat and protein percentages despite the increase in total milk production. In fact, cows with the marker increased protein percentage. This is unexpected because traditionally, as milk production increases, fat and protein percentage will decrease. (Welper, R. D. and Freeman, A. E.,(1992), Genetic Parameters for Yield Traits of Holsteins, Including Lactose and Somatic Cell Score, J Dairy Sci. 75: 1342–1348), incorporated herein by reference. The article discloses data collected from first lactations of 5246 cows. The data clearly evidences the negative correlation between fat and protein percentages and total milk production.

TABLE 2

Population Data (Adapted from Welper
and Freeman, J.D.S., 1992, page 1347)

| | Fat | Protein | Fat % | Protein % |
|---|---|---|---|---|
| Milk | .81 | .96 | −.34 | −.36 |
| Fat | | .85 | .27 | −.06 |
| Protein | | | −.20 | −.09 |
| % Fat | | | | .51 |

As can be seen (Table 2), as pounds of milk go up, pounds of protein and fat will increase, but the percentage of fat and protein per pound of milk will decrease. It is also traditionally characteristic for cows to produce more fat than protein.

This traditional characterization holds true when cows from the entire research herd used for this study are grouped regardless of the PIT-1 genotype.

TABLE 3

Overall phenotypic correlations from the ISU
breeding research herd. This includes all
cows, both those with and without the PIT-1
genotype.

| | Fat | Protein | Fat % | Protein % |
|---|---|---|---|---|
| Milk | .78 | .95 | −.20 | −.31 |
| Fat | | .82 | .44 | .03 |
| Protein | | | −.06 | .00 |
| % Fat | | | | .49 |

As can be seen (Table 3), the characteristic relationships are present. As illustrated in Table 1, the cows with the marker reversed these normal relationships, maintaining and even increasing fat and protein content with an increase in overall milk production.

This effect of the marker is also dramatically demonstrated by comparing milk content for the highest milk producing quarter of the herd with the lowest producing quarter (Table 4). When the grouping is done regardless of the marker lower fat and protein percentages are observed with the high milk producers.

TABLE 4

Comparison of the whole herd (including
and excluding the PIT-1 genotype) by
highest and lowest quartiles.

| | Milk | Fat | Protein | % Fat | % Protein |
|---|---|---|---|---|---|
| Highest 25% | 27,047 | 883 | 827 | 3.08 | 3.06 |
| Lowest 25% | 17,313 | 576 | 558 | 3.16 | 3.22 |

Quite unexpectedly, when the marker is used to separate cows; in cows with the marker there is an increase in total milk production, fat and protein, with the percentages of fat and protein per pound of milk remaining the same or even increasing over cows without the PIT-1 marker allele.

Thus, cows with the marker exhibited an average 13.2% of increase in total milk production, a 12.6% increase in total pounds of fat and a 17.2% increase in total protein content. As for content per pound of milk the percentage of fat per pound of milk remained the same and the percentage of protein even increased. This is so despite the expected negative correlation between the percentages and total milk, and is an unexpected result. Thus more milk is generated that is qualitatively as good or better; rather than more milk with fewer (lower %) nutrients as in traditional programs.

EXAMPLE 2

Cloning of Bovine Pit-1 Chromosomal Region

The PIT-1 chromosomal region was cloned and subjected to extensive analysis. Recombinant phage have been identified carrying one of each allele i.e. both alleles are represented in the collection of clones obtained. The genomic region isolated extended for approximately 16 kilobasepairs (kbp) encompassing the region contained in the polymorphic HinfI restriction fragments (exons 4 and 6 see FIG. 1) as well as a large amount of DNA surrounding these fragments.

Screening and cloning of the bovine PIT-1 gene was performed as follows. First a bovine genomic library from adult male liver was purchased (CLONTECH, Inc.). The average insert size was 16 kb, the range was from 8–21 kb fragments. The library was grown on K802 *E. coli* cells on 150 mm petri plates. The number of independent clones screened were approximately 576,000 pfu's.

The clones were then transferred to nitrocellulose filter (Schleicher & Schuell, 137 mm, 0.45 um) using standard techniques (Sambrook, et al. 1989).

A UV Stratalinker was used to fix the DNA to the filter. The filters were then partially dried and stored at 4° C.

A radio-labeled probe was made using the Stratagene Prime-It II Random Oligonucleotide Primer Labelling Kit. Six probe labelling reactions were conducted, three with each fragment. (HindII-PstI fragment from RSV BGHFI plasmid and EcoRI fragment from bG0.67 plasmid) a total of 150 ng of probe. The probe was then hybridized with the filters by first performing a pre-wash twice for one hour each time 150 ml at 42° C. using 10X Denhardt's, 5xSSC, 0.1% SDS and 0.1% NaPOP. Then Pre-Hybridization was completed by 4 hours in 150 mls at 37° C. in 43% formamide, 5x SSC, 10x Denhardt's, 0.1% SDS, 0.1% NaPOP, 100 µg/ml sonicated Salmon Sperm DNA. Hybridization was conducted for 18 hours, 105 mls at 37° C. in the same as the pre-hybridized solution with added boiled probe, 1.7 million counts per ml.

Then filters were rinsed at room temperature in 2x SSC and 0.1% SDS. After rinsing the filters were washed twice for 20 minutes at 60° C. in 0.5xSSC/0.1% SDS and once for 15 minutes at 60° C. in 0.5xSSC/0.1% SDS. The resulting hybridized probe filter complex was exposed to X-ray film overnight (for 18 hours) at −70° C. (freezer). For results 8 clear positives were found and cored using pasteur pipettes and placed in 500 µl SM buffer.

As a secondary screening procedure, each positive primary lysate was plated on 150 mm petri plates (500–800 pfu's per plate) and using the same procedures as the primary screen identified positive single plaques and cored and resuspended in these 500 µl SM buffer at 4° C. overnight. Each secondary clone was titered and amplified to obtain enough titer for large plate lysates. Large lysate preparations of isolated clones was done as described (Sambrook, et al., (1989)).

The phage DNA was isolated using Qiagen Lambda preps from the large lysate preparations. Yield was from 5 to 17 µg DNA resuspended in 100 µl TE buffer at pH 8.0.

The 13 kb XhoI fragments from both alleles, the marker allele EcoRI 4.5 and 1.4 kb fragments and the marker allele 800 and 600 bp HinfI fragments were subcloned into pBluescript SK+ plasmid vector into the XhoI, EcoRI, and Filled in HinfI sites respectively.

First the EcoRI and HinfI subcloned fragments were sequenced by using plasmid primers. Then the 13 kb subclones and the 4.5 EcoRI subclones were restriction mapped. Finally internal primers for sequencing the two allelic 13 kb subclones were designed. See FIG. 1 for relation of primers to PIT-1 regions. The sequences derived are disclosed in FIGS. 3 and 4. (SEQ ID NO: 1 and 2)

| SEQUENCE OF PRIMERS USED FOR SEQUENCING THE GENOMIC REGION OF BOVINE PIT-1 | | |
|---|---|---|
| JW 871 | TAAAGACGCT GAAAACACCT | (SEQ ID NO: 5) |
| JW 872 | TACTTGCTCG GCTTCCTC | (SEQ ID NO: 6) |
| JW 929 | AGACCAGCCT AAATCAGAGT T | (SEQ ID NO: 7) |
| JW 936 | GGGAAAGTTT CTACACAATG | (SEQ ID NO: 8) |
| JW 963* | AAACCATCAT CTCCCTTCTT | (SEQ ID NO: 3) |
| JW 964 | GATTTGGCTC CACTATTGTA | (SEQ ID NO: 9) |
| JW 987* | AATGTACAAT GTGCCTTCTG AG | (SEQ ID NO: 4) |

Figure 2:
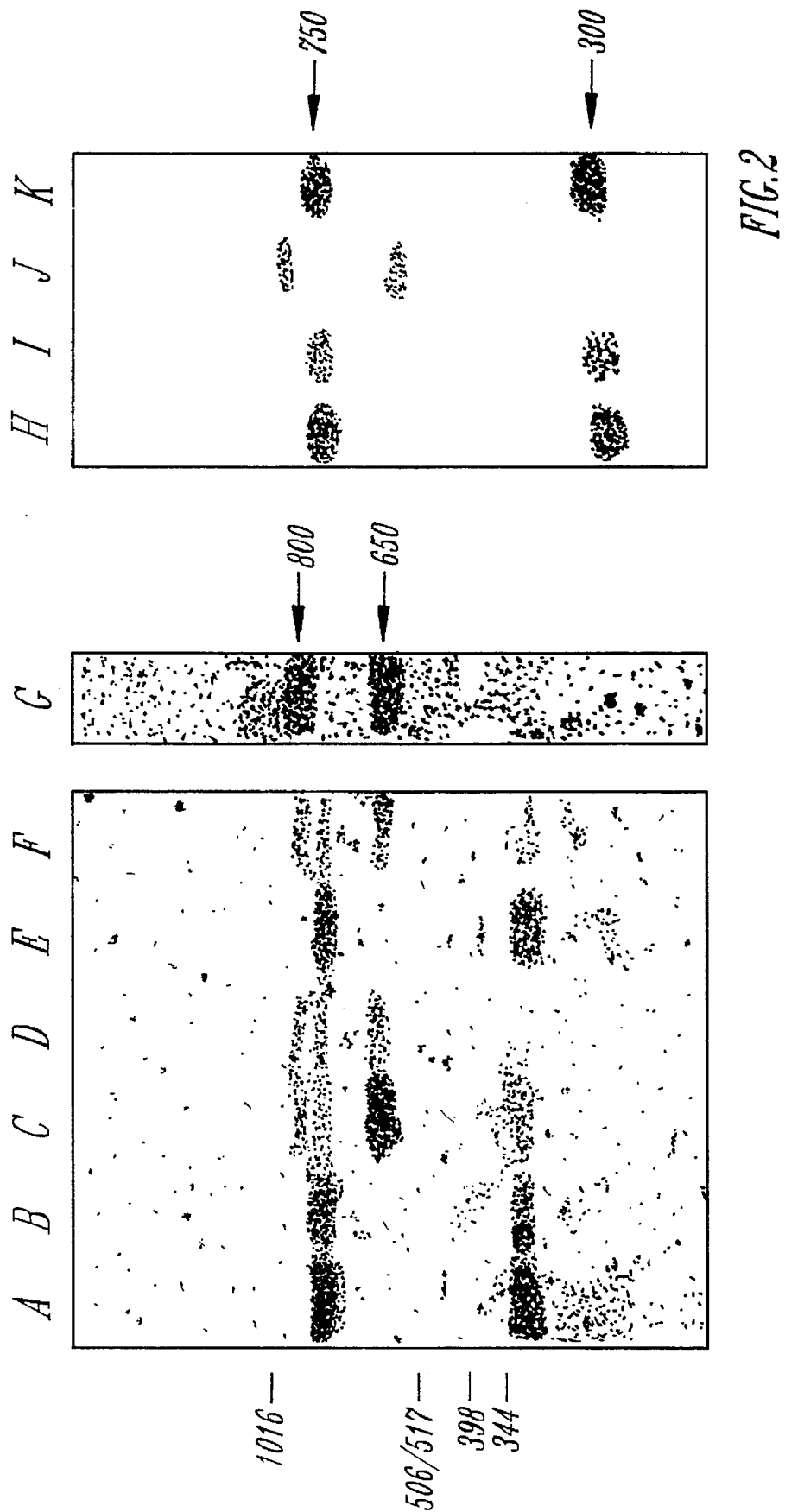
FIG. 2 is a representative comparison of the HinfI pattern with several animals by standard southern blotting of genomic DNA (left) and the HinfI pattern from various recombinant bacteriophage carrying the PIT-1 chromosomal region (right). Patterns were detected with the bovine PIT-1 cDNA. Three patterns are seen with the genomic DNA samples; (A) two bands at 800 base pairs (bp) and 650 bp; (B) two bands at 750 bp and 300 bp; or (C) all four bands.

*primers used in the PCR test in exon 6.
All sequences listed in 5' to 3' direction A 13 kbp EcoRI fragment was subcloned from the bacteriophage for each genotype and restriction mapped. FIG. 2 shows a comparison of the HinfI pattern with several animals by standard Southern blotting of genomic DNA (left) and the HinfI pattern from various recombinant bacteriophage carrying the PIT-1 chromosomal region (right).

Lanes A–G are seven different animal's genomic DNA digested with HinfI, electrophoresed, transferred to nitrocellulose and probed with radioactively labeled bovine PIT-1 cDNA. Lanes H–K are four different recombinant lambda clones which were isolated from the screening of the bovine library (as phage hybridizing to the PIT-1 cDNA probe). Clone DNA was isolated from phage preparations per standard protocols, digested with HinfI, and detected as above.

At the left, approximate locations and specific sizes of molecular weight markers are given; at the right in each figure is approximate sizes of specific HinfI restriction fragments based on the relative mobilities of the known sizes of the molecular weight markers. The right gel (lanes H–K) was electrophoresed slightly longer than the left gel (lanes A–G).

Note that the HinfI enzyme in chromosomal DNA from animals and hybridization with PIT-1 cDNA detects two to four bands, depending on the animal's genetic makeup of the two copies of the PIT-1 gene it carries (diploid). This system detects only two bands in the individual lambda clones, since they have either one genotype or the other (haploid). This result indicates that we have clones that together can combine to make the patterns observed in the cow DNA; lanes A, B and E are from animals that have the same pattern as H, I and K, indicating they have only one type of PIT-1 gene. Lane G is from an animal that has the same pattern as Lane J, indicating it has only one type of PIT-1 gene, and this gene is different in HinfI sites from the gene form seen in A, B and E animals. In lanes C, D and F, these animals are interpreted as having one copy of each form of the PIT-1 gene seen above.

Thus three patterns are seen with genomic DNA samples. (a) two bands, one at approximately 800 and one at approximately 650; (b) two bands, one at approximately 750 and one at approximately 300; or (c) all four bands. These patterns represent three possible genotypes in a two-allele polymorphic single locus where the (a) and (b) genotypes are homozygous and the (c) genotype is heterozygous. In the clone DNA analysis where only one form of DNA per clone is possible, all genotypes are present. The genotype marker was seen in a clone marked 56, while other clones had the non-marker genotype.

The HinfI fragments from the "marker" genotype 13 kbp clone (clone BPX56) which hybridized to the bovine cDNA probe were isolated and sequenced (FIGS. 3, 4, SEQ ID NO: 1 and 2). Primary structural information from the sequencing allowed additional primers to be synthesized in order to sequence the corresponding regions in the 13 kbp clone of the other PIT-1 allele (clone BPX78). This analysis allowed comparison of the genetic structure of the two genotypes and preliminary analysis of one HinfI fragment indicated that the 3' HinfI site at nucleotide 630 in SEQ ID NO: 1 and within exon 6 COOH-terminal coding region (FIG. 4) (SEQ ID NO: 2) is different between clone 56 and clone 78. The sequencing of clone 56 is AGACAAGCCTAAATCAGAGTT (FIG. 4B) (SEQ ID NO: 2) while in clone 78 (FIG. 4C) (SEQ ID NO: 2) the sequence in this region is AGACAAGCCTGAATCAGAGTT where the GAATC sequence in bold is the HinfI recognition sequence. There is also a corresponding change in the codon in this region (from CTA to CTG, underlined above). It should be noted that the amino acid encoded by the triplet, Leucine, does not change due to the degeneracy in the genetic code. However the sequence difference does change this codon from a rarely used Leucine codon (4.9% utilization in bovine genes) to the most commonly used Leucine codon (46.6% utilization).

EXAMPLE 3

PCR Amplification Test

Figure 5:
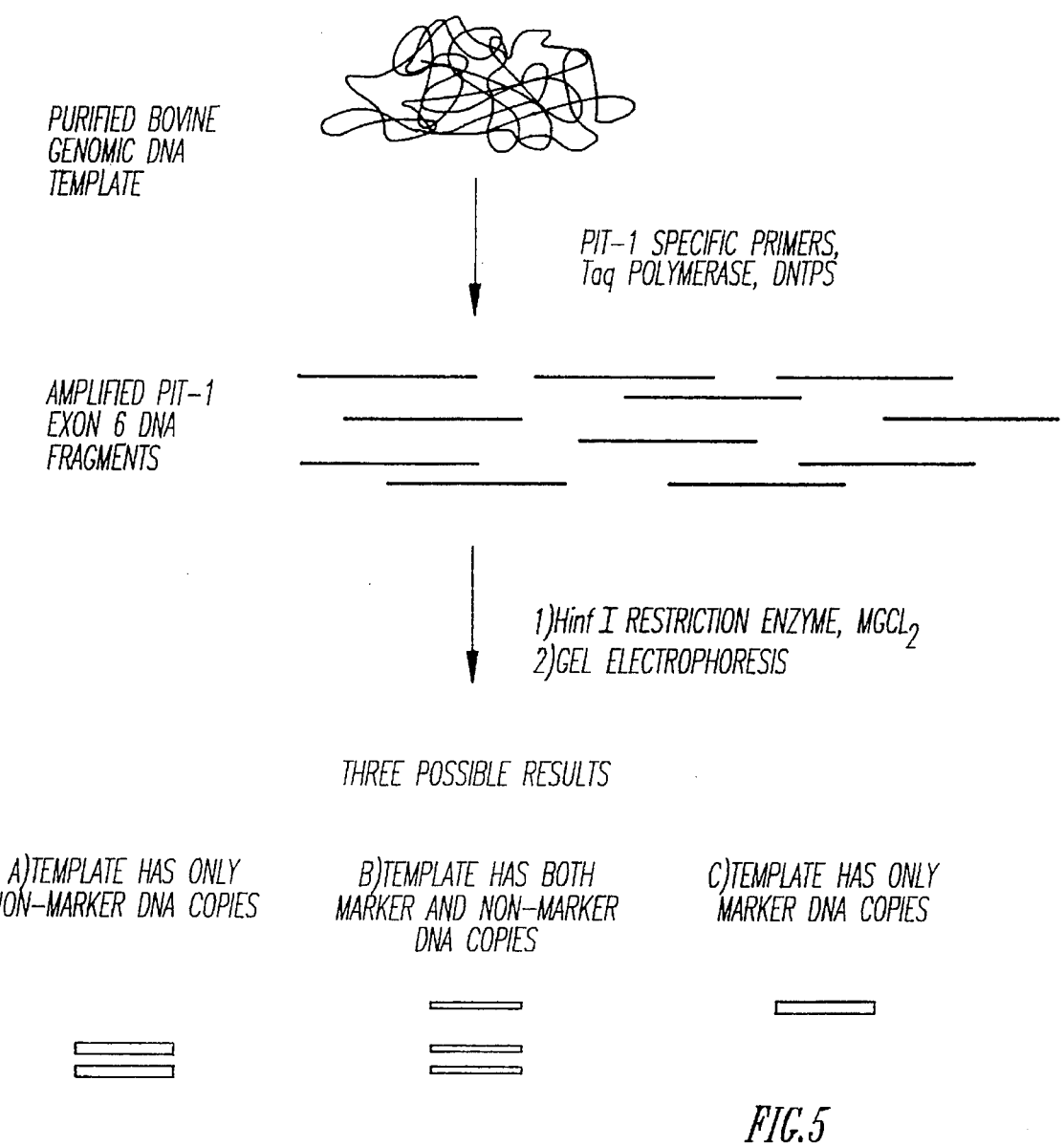
FIG. 5 is a schematic depicting the PIT-1 polymorphism PCR test.
Figure 6A:
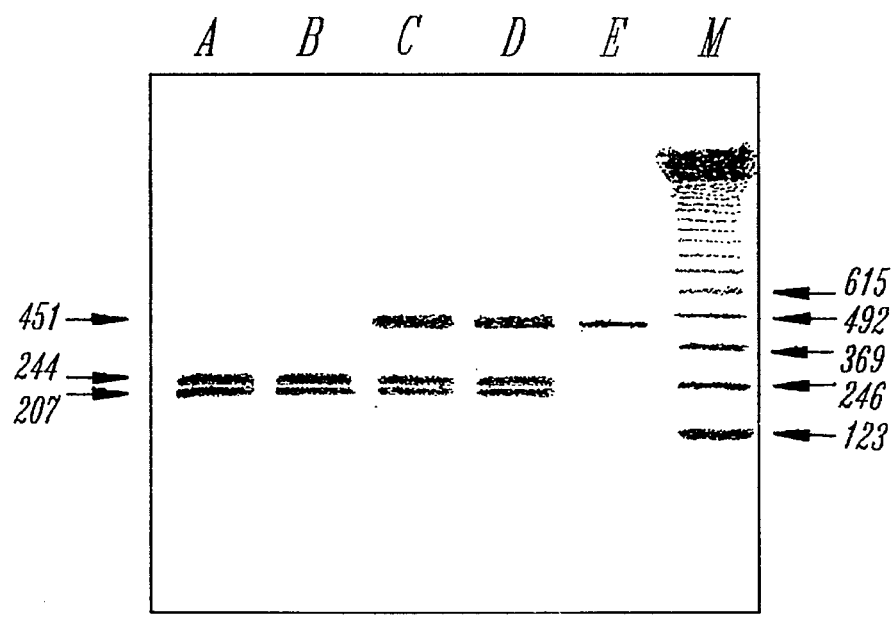
FIGS. 6A–6D are the results of the PCR test demonstrating ability to detect both alleles.
Figure 6B:
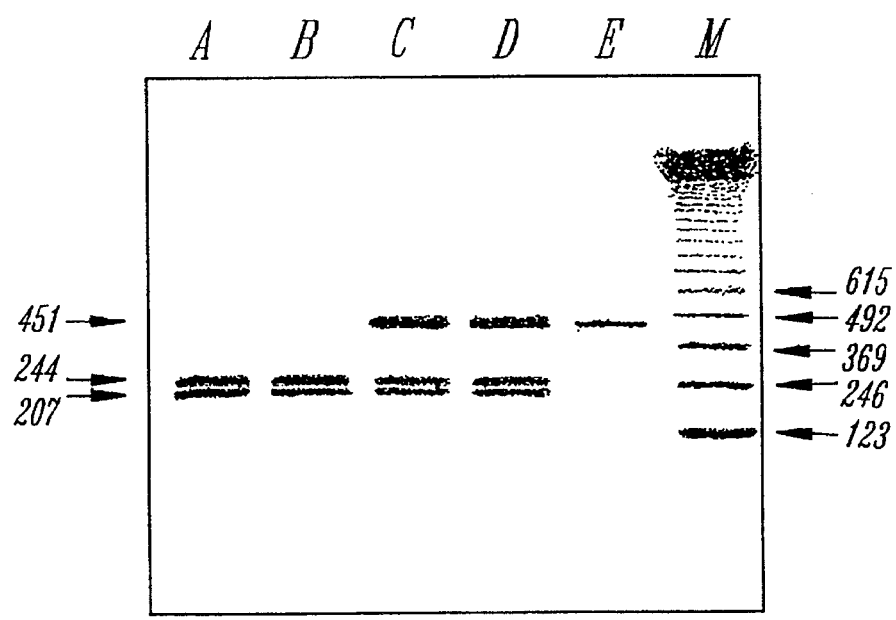
Figure 6C:
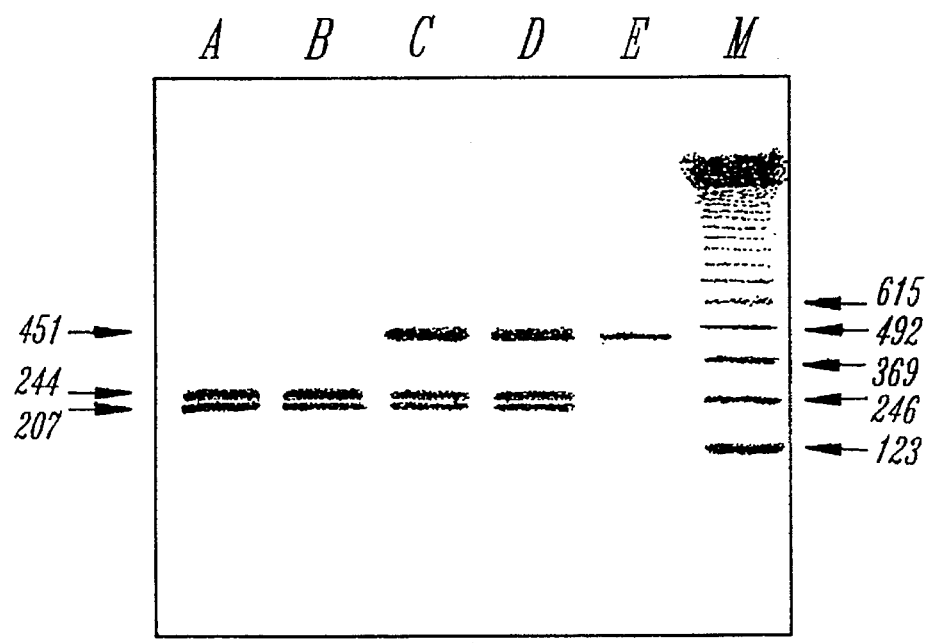
Figure 6D:
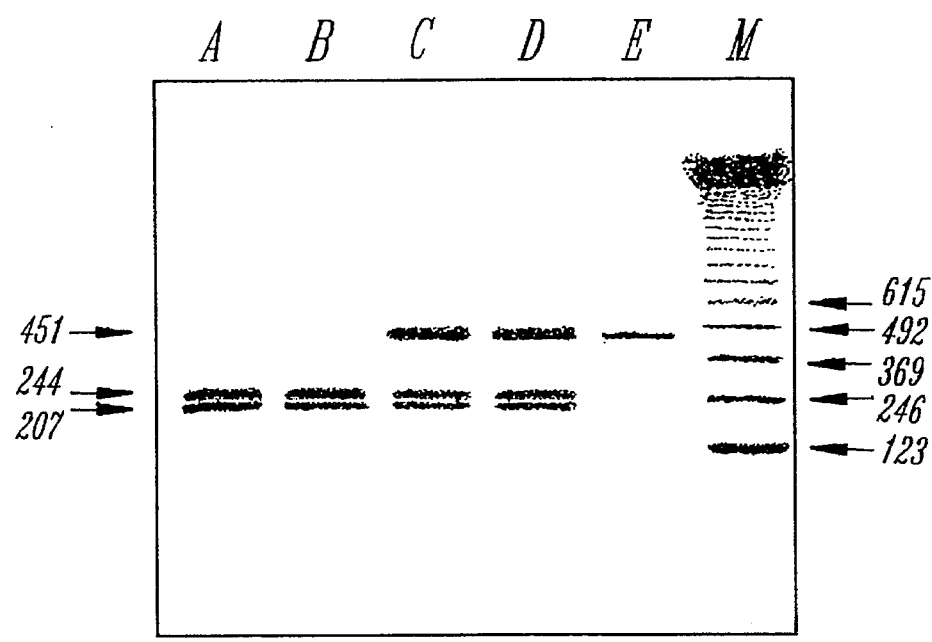

Analysis of the intronic regions of bovine PIT-1 and sequence data has allowed for provision of an in vitro amplification system which may be used for detection of the exon 6 HinfI polymorphism by PCR and later HinfI digestion of the PCR products. (See FIGS. 5 and 6).

A method was developed using PCR amplification to rapidly screen animals for the mutation at position 165 in exon 6 (position 630 in SEQ ID NO: 2) so that animals genetic status with respect to the marker for increased milk product could be conclusively and quickly determined. The method involves DNA amplification using nucleotide primers which are specific to regions adjacent to the nucleotide position of the polymorphic HinfI site in exon 6. The primers selected are illustrated in FIG. 4 (SEQ ID NO: 2) and include intronic sequences on either side of exon 6. The 5' primer sequence was 5'-AAACCATCATCTCCCTTCTT-3' (SEQ ID NO: 3) which corresponds to nucleotides 424–443 (SEQ ID NO: 2). The 3' primer sequence was 5'-AATGTACAATGTGCCTTCTGAG-3'(SEQ ID NO: 4) which corresponds to the complement of nucleotides 853–874 (SEQ ID NO: 2). Nucleotide primers such as these may be derived from other sequences in the PIT-1 gene or from the novel intronic sequences disclosed in this application.

The PCR protocol developed using these two primers includes the following. First genomic DNA was isolated from blood by methods generally known to those of skill in the art. Next the concentration of DNA was measured by dilution of DNA in water and reading Absorbance at 260 nm wavelength in a UV-vis spectrophotometer. DNA concentration was calculated by multiplying the dilution factor and the conversion factor 50 µg DNA per ml has Absorbance at 260 nm of 1.0. Then a mixture was prepared of the following solutions in a 0.5 ml microcentrifuge tube:

5 µl 10×PCR buffer

8 µl dNTP solution (1.25 mM each of dATP,dTTP, dCTP, dGTP)

4 µl MgCl₂ solution (0.025M)

4 µl primer A (5'AAACCATCATCTCCCTTCTT3') 5 pmoles/µl (SEQ ID NO: 3)

4 µl primer B (5'AATGTACAATGTGCCTTCTGAG3') 5 pmoles/µl (SEQ ID NO: 4)

22 µl distilled, autoclaved water 0.5 µl Taq DNA polymerase (5.0 u/µl)

2.5 µl genomic DNA template (0.25 µg)

total: 45 µl

The solution was overlayed with mineral oil to prevent evaporation. Tubes were placed in a thermocycler unit programmed as follows:

1. 95° C. for five minutes to denature DNA
2. 95° C. for 30 seconds
3. 56° C. for one minute
4. 72° C. for two minutes
5. Cycle back to step 3 and cycle for 34 times (a total of 35 repetitions of steps 3–5).
6. 72° C. for five minutes
7. 4° C. for indefinite time (storage temperature until HinfI digestion step).

For those reactions with sufficient product to analyze, a 5–10 µl aliquot (depending on the relative concentration of PCR product) was removed and added to a 1.5 ml microcentrifuge tube with 3 µl 10×buffer (New England Biolabs restriction digest buffer #2); 2 µl HinfI (10 units/µl, New England Biolabs, Inc). Distilled water was added to adjust final volume to 30 µl. The reaction was incubated at 37° C. for 4 to 16 hours. Finally the restriction digests were analyzed in agarose gels containing ethidium bromide at 1 mg/µl.

The PCR product amplified is 451 basepairs (bp) in length. The HinfI enzyme can digest the 451 bp fragment into two fragments of 244 bp and 207 bp but only in DNA amplified from non-marker genotype DNA. Thus all three genotypes can be detected by the test; complete cutting of PCR product indicates the animal does not have any copies of the marker gene, 50% cutting indicates the animal has one copy of each genotype, and no cutting indicates the animal has two copies of the marker gene. FIG. 6 shows the results.

The figure shows a 2% agarose gel in which various HinfI-digested PCR products from cows and cloned DNA were separated. Detection is by ethidium bromide staining as described in the methods. Molecular weight marker is the 123 bp ladder from BRL, Inc. Shown at the left is the predicted sizes of uncut (451) and cut DNA fragments (244, 207), and at the right the known sizes of the molecular weight marker. Note that different HinfI patterns are observed; complete cutting (lanes A and B, no marker genotype animals), 50% cutting (lanes C and D, heterozygous animals). The template in lane E is the cloned 13 kbp fragment from the BPH 56 phage, and is the uncut size control.

Finally comparison was made between sequence identifications made by the PCR test and exon 6 with the Southern hybridization test for 15 cows. In all 15 cases the two tests agreed completely indicating that the clone DNA and the differences identified are precisely correct at the PIT-1 in the bovine chromosome. The comparisons were done in a double blind manner; tests on individual animals were scored separately and the test results were then compared. It must be noted that the primers used from this are simply selected primers of 12–30 contiguous nucleotides on either side of exon 6 and the selection of other primers within the novel region sequenced by applicant may be used, as well as primers obtained from cDNA.

Thus from the foregoing it can be seen that the invention accomplishes at least all of its objections.

What is claimed is:

1. A method of identifying a bovine which possesses a genotype indicative of improved milk production traits, said method comprising:

obtaining a nucleic acid sample from said bovine and identifying a polymorphism characterized by nucleotide position 165 in exon 6 of the bovine PIT 1 gene, wherein the presence of an adenine is associated with improved milk production traits.

2. The method of claim 1 wherein said step identifying comprises restriction fragment length polymorphism analysis.

3. The method of claim 1 further comprising the step of:

amplifying said bovine PIT-1 gene sequence.

4. The method of claim 3 further comprising the step of digesting said amplified region with the restriction endonuclease Hinf I.

5. The oligonucleotide of claim 3 wherein primers selected from the group consisting of: SEQ ID NO: 3 and SEQ ID NO: 4 are used in said amplification.

6. A single strand of oligonucleotide primer useful for detecting nucleotide 165 of exon 6 of a bovine PIT-1 gene said primer consisting of a nucleotide sequence having about 12–30 contiguous bases from SEQ ID NO: 2.

7. The oligonucleotide of claim 6 wherein said oligonucleotide has the nucleotide sequence represented by SEQ ID NO: 3.

8. The oligonucleotide of claim 6 wherein said oligonucleotide has the nucleotide sequence represented by SEQ ID NO: 4.

9. A method of identifying a bovine which possesses a genotype indicative of improved milk production traits, said method comprising:

obtaining a sample of genomic DNA;

digesting said sample with Hinf I;

separating the fragments obtained from said digestion;

identifying the presence or absence of a Hinf I site at base 165 of exon 6 of the bovine PIT-1 gene wherein the absence of said site is associated with improved milk production.

10. The method of claim 9 further comprising the step of:

selecting said cattle with said genotype for breeding.

11. The method of claim 9 wherein said polymorphism is identifiable by an 800 bp RFLP when a restriction enzyme which cuts at the same recognition sites as HinfI is used.

12. The method of claim 8 wherein said step of identifying includes:

detecting said Hinf I site by amplification.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1002 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 561..726

( i x ) FEATURE:
        ( A ) NAME/KEY: intron
        ( B ) LOCATION: 1..560

( i x ) FEATURE:
        ( A ) NAME/KEY: intron
        ( B ) LOCATION: 727..1003

( x i ) SEQUENCE DESCRIPTION: SEQ ID NO:1:

```
CTGAATCAGT  CCCTGGGTTG  GGAAGATCCC  CTGGAGCTGG  GAACAACCTA  CCNAACCAGA    60
TTCTGGCCTG  GAGAATTCCA  TGTACTGTAT  AGTCCATGGG  GTTCCAAAGA  ATAGTCTGAC   120
TACACTTATA  TTAGGTTATA  AAAATGATTC  ATGTATAATT  ACTACAGTAT  ATAGCCCAGT   180
GGCAAAAAAA  TAAATCTGGA  TACATTAAAA  AGCATTTCAC  TACTTTATAC  CTATGCTACA   240
TTGTCTAGAA  ACTTTTCTTA  TATATTTGTG  CAAAGTGTGT  TTAACACATT  TATCCAGTTT   300
GGCTAAATAT  GAATGGCAGA  TGTTCCTATC  TGAATTCTTT  TGGCTTCTAA  AATATTAACT   360
TATTAACTAG  AAGGAATTTT  TTAAAATACT  AGACAATTCT  ACACTGAATA  ACCTTACTGT   420
TATTCTAAAT  TGCTAACAAA  TATATCGTTA  AAAGCAATAT  TTAATAGTTG  ACAAAAATAC   480
TACACAAATT  TATACAATAG  TGGAGCCAAA  TCAGTGTTTC  TTGCAAAACT  GAAGCTGATG   540
GCCTTTGTTA  TTCTTTCACA  GGATACACCC  AGACAAATGT  TGGGGAAGCT  CTGGCAGCTG   600
TGCATGGCTC  TGAATTCAGT  CAAACAACTA  TCTGCCGATT  TGAAACCTG   CAGCTCAGCT   660
TCAAAAATGC  ATGCAAACTA  AAAGCAATAT  TATCCAAATG  GCTGGAGGAA  GCCGAGCAAG   720
TAGGAGGTAC  AAAAGCTGTG  TTTCTGGAAA  CAGTGATGTT  TTAACCTAAA  AACAATGGTT   780
TCCCTCAGTT  GAATTTGTGC  TAAAGCGAGA  GGTTTGAAGT  TTGGTTTGGA  TTTTTCTCTT   840
TGACATGAAA  AATAAGTATC  TTGTTTCATC  ACACTATGAA  GAAAAGCAAG  GCCAGTGAAA   900
GTGTAGAAAT  AAATTTATTG  AGAAGGTAAA  TAATGAGAGA  ATAAAATATA  TAGGGAAAGT   960
TTCTACACAA  TGTGGCATAG  GTGTGAAGTG  GTGAAATGAT  TC                      1002
```

( 2 ) INFORMATION FOR SEQ ID NO:2:

( i ) SEQUENCE CHARACTERISTICS:
        ( A ) LENGTH: 972 base pairs
        ( B ) TYPE: nucleic acid
        ( C ) STRANDEDNESS: single
        ( D ) TOPOLOGY: linear ( i i ) MOLECULE TYPE: DNA (genomic)

(  i i i  ) HYPOTHETICAL: NO (  i v  ) ANTI-SENSE: NO (  i x  ) FEATURE:
    ( A ) NAME/KEY: CDS
    ( B ) LOCATION: 466..678

(  i x  ) FEATURE:
    ( A ) NAME/KEY: allele
    ( B ) LOCATION: replace(630, "g")

(  i x  ) FEATURE:
    ( A ) NAME/KEY: intron
    ( B ) LOCATION: 1..465

(  i x  ) FEATURE:
    ( A ) NAME/KEY: intron
    ( B ) LOCATION: 679..972

(  x i  ) SEQUENCE DESCRIPTION: SEQ ID NO:2:

| | | | | | | |
|---|---|---|---|---|---|---|
| ATGACTTCTA | GCATTTCAAG | CCAGATTGTT | CAATTTATCT | TTTTGTAGTT | TCCGTGAGGC | 60 |
| TCATGGAGGA | ATTGCTAATA | NACAGGTTTT | GTTTTGGNTG | GNTAGTTGTA | CACTAAACAT | 120 |
| TTCAATAACC | TGAGTTCTGG | GGGACATTTA | GAAATGCATA | CAGAATTATT | TTCTTCTCAG | 180 |
| TAAGTCAGTG | CCCTCTTGTG | GCAGAAAGTG | GATAAACAAT | GTCGGGGTTC | CCTCCCTAAT | 240 |
| TTCTTCCTGT | GACTCTGGTA | AAAGGAGCCT | ACATGAGACA | AGCATCTAAA | TGTTCAAAAA | 300 |
| AACTTCACAT | TTATTATTGT | TGAAAAGCTT | TGAAGGTGTT | TTCAGCGTCT | TTAGGTTTCC | 360 |
| TTTTTACGTT | AATGTTAGTA | CTAATATTTA | GGAAATGTAA | CCTAACTTGA | TTTTAATGGG | 420 |
| CCTAAACCAT | CATCTCCCTT | CTTTCCTGCC | AACTCCCCAC | CTCCAGTAT | TGCTGCTAAA | 480 |
| GACGCCCTGG | AGAGACACTT | TGGAGAACAG | AATAAGCCTT | CCTCTCAGGA | GATCCTGCGG | 540 |
| ATGGCTGAAG | AACTAAACCT | GGAGAAAGAA | GTGGTGAGGG | TTTGGTTTTG | TAACCGAAGG | 600 |
| CAGAGAGAAA | AACGGGTGAA | GACAAGCCTA | AATCAGAGTT | TATTTACTAT | TTCTAAGGAG | 660 |
| CATCTCGAAT | GCAGATAGGC | TCTCCTATTG | TGTAATAGCG | AGTGTTTCTA | CTTTTCATTC | 720 |
| CTTTCTCTTC | TCCAGCCAAA | ATAGAAATTA | GTTATTTGGT | TAGCTTCAAA | AAATCACATC | 780 |
| AGTAATTTTG | GCAGAAGTGT | TTCTTTTCTA | CTTTAAAAAT | AAATACAATT | TAAATTATGT | 840 |
| TGATGAATTA | TTCTCAGAAG | GCACATTGTA | CATTTTAAGC | CAAAGACTAA | TAGGATTAAA | 900 |
| ACAATGATTC | TGTCCCTTTC | ACTATATCTT | TCCCTCTATC | TCTCCCTAAC | ACACACACAC | 960 |
| ACACACACAC | AG | | | | | 972 |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

AAACCATCAT CTCCCTTCTT                                                       20

( 2 ) INFORMATION FOR SEQ ID NO:4:

( i ) SEQUENCE CHARACTERISTICS:

(A) LENGTH: 22 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

AATGTACAAT GTGCCTTCTG AG    22

(2) INFORMATION FOR SEQ ID NO:5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

TAAAGACGCT GAAAACACCT    20

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

TACTTGCTCG GCTTCCTC    18

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

AGACCAGCCT AAATCAGAGT T    21

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GGGAAAGTTTC TACACAATG 20

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

GATTTGGCTC CACTATTGTA 20